United States Patent
Creevy

(10) Patent No.: US 8,173,147 B2
(45) Date of Patent: May 8, 2012

(54) GENTLE, NON-IRRITATING, NON-ALCOHOLIC SKIN DISINFECTANT

(75) Inventor: Kevin Scott Creevy, Winnetka, IL (US)

(73) Assignee: Xttrium Laboratories, Inc., Chicago, IL (US)

( * ) Notice: Subject to any disclaimer, the term of this patent is extended or adjusted under 35 U.S.C. 154(b) by 898 days.

(21) Appl. No.: 12/192,502

(22) Filed: Aug. 15, 2008

(65) Prior Publication Data

US 2010/0040657 A1 Feb. 18, 2010

(51) Int. Cl.
*A01N 25/00* (2006.01)

(52) U.S. Cl. ........................... 424/405; 424/401

(58) Field of Classification Search ................ None
See application file for complete search history.

(56) References Cited

U.S. PATENT DOCUMENTS

| | | |
|---|---|---|
| 3,855,140 A | 12/1974 | Billany et al. |
| 3,960,745 A | 6/1976 | Billany et al. |
| 4,374,126 A | 2/1983 | Cardelli et al. |
| 4,420,484 A | 12/1983 | Gorman et al. |
| 4,919,837 A | 4/1990 | Gluck |
| 4,956,170 A | 9/1990 | Lee |
| 5,164,107 A | 11/1992 | Khan et al. |
| 5,422,029 A | 6/1995 | Potini et al. |
| 5,500,144 A | 3/1996 | Potini et al. |
| 5,641,498 A | 6/1997 | Loosemore |
| 5,719,113 A | 2/1998 | Fendler et al. |
| 5,763,412 A | 6/1998 | Khan et al. |
| 5,776,430 A | 7/1998 | Osborne et al. |
| 5,980,925 A | 11/1999 | Jampani et al. |
| 6,017,516 A | 1/2000 | Mody et al. |
| 6,107,261 A | 8/2000 | Taylor et al. |
| 6,136,771 A | 10/2000 | Taylor et al. |
| 6,204,230 B1 | 3/2001 | Taylor et al. |
| 6,383,505 B1 | 5/2002 | Kaiser et al. |
| 6,444,745 B1 | 9/2002 | Kilgour et al. |
| 6,531,540 B1 | 3/2003 | O'Brien |
| 6,538,061 B2 | 3/2003 | Chaiyawat et al. |
| 6,759,479 B2 | 7/2004 | O'Brien |
| 2003/0165546 A1* | 9/2003 | Resch et al. ................ 424/401 |
| 2004/0102429 A1* | 5/2004 | Modak et al. ............... 514/184 |
| 2005/0191247 A1 | 9/2005 | Drake et al. |
| 2006/0141017 A1* | 6/2006 | Kling et al. ................. 424/445 |
| 2007/0025948 A1 | 2/2007 | Saito |
| 2007/0184114 A1* | 8/2007 | Cevc ........................... 424/484 |
| 2008/0102050 A1* | 5/2008 | Li et al. .................... 424/70.12 |
| 2008/0247972 A1* | 10/2008 | Conceicao ................... 424/52 |

FOREIGN PATENT DOCUMENTS

| | | |
|---|---|---|
| CA | 2 285 967 | 10/1998 |
| EP | 0604848 | 6/1994 |
| EP | 0934742 | 11/1999 |
| WO | WO 03034994 | 5/2003 |
| WO | WO03075883 | 9/2003 |
| WO | WO2008033286 | 2/2008 |
| WO | WO2009050447 | 4/2009 |

OTHER PUBLICATIONS

Xttrium Laboratories Product Brochure [online], [retrieved on Jul. 30, 2008] Retrieved from the Xttrium Laboratories Website using Internet <URL: http://www.xttrium.com/list_product.aspx.

Momentive Performance Materials, "Sun Care Solution Finder" [online] [retrieved on Oct. 10, 2008] Retrieved from website using Internet <URL: http://www.momentive.com/geam/gesa/personalcare/PDFs/Sun%20Care%20Solutions[1].indd.pdf.

Johnson & Johnson Medical PTV. LTD., "Microshield *Skincare Products, Microshield *4 Chlorhexidine Surgical Handwash" [online] [retrieved on Oct. 10, 2008] Retrieved from website using Internet <URL: http://www.infectioncontrolsolutions.com/ics/pdfs/MICROSHIELD_4_BROCHURE.pdf.

International Search Report mailed Nov. 10, 2008 for related International Application No. PCT/US08/73368.

European Search Report and Written Opinion issued in corresponding EU Patent App. No. 08798013.2.

* cited by examiner

*Primary Examiner* — Bethany Barham
(74) *Attorney, Agent, or Firm* — Duane Morris LLP

(57) ABSTRACT

The present invention relates to leave-on antimicrobial compositions that provide a substantial reduction in Gram-positive and Gram-negative bacteria without the use of alcohol as either a vehicle or a secondary active ingredient.

31 Claims, No Drawings

GENTLE, NON-IRRITATING, NON-ALCOHOLIC SKIN DISINFECTANT

TECHNICAL FIELD OF THE INVENTION

The present invention relates to antibacterial and antiseptic compositions.

BACKGROUND OF THE INVENTION

In recent years there has been a dramatic increase in the prevalence of antibiotic-resistant microorganisms. There is considerable concern in the medical community about penicillin resistant pneumococci, vancomycin resistant enterocci and methicillin and quinolone resistant *Pseudomonas aeruginosa*. Since the early 1980's in the United States and Europe, the incidence of infection by methicillin resistant *Staphylococcus aureus* (MRSA) and the vancomycin resistant enterococci (VRE) have increased substantially. In medical intensive care units around the country, increased colonization of vancomycin resistant *enterococcus* has recently reached epidemic proportions. These microorganisms survive by the colonization of the natural environment and new patients through cross contamination. Diarrhea and fecal incontinence further increase the risk of skin colonization by VRE, suggesting that skin colonization is associated with increased risk of catheter related sepsis, cross-infection, and blood culture contamination.

These findings suggest that in order to minimize VRE skin contamination the bacterial contamination of health care workers' hands must be reduced, thus interrupting transmission between patients.

*Staphylococcus aureus* is a major cause of nosocomial infections including: bloodstream infections, surgical site infections, and pneumonia. Summary data maintained by the Center for Disease Control demonstrated that from January 1990 through May 1999, *Staphylococcus aureus* infections accounted for: 12.6% of intensive care unit (ICU) acquired bloodstream infections, 18.1% of ICU acquired cases of pneumonia, and 16% of ICU acquired urinary tract infections. Surveillance reports indicate that further development of resistance by *Staphylococcus aureus* has increased rapidly in recent years and that the overall proportion of *Staphylococcus aureus* isolates resistant to methicillin in participating hospitals increased from 2.4% in 1975 to 29% in 1991.

Methicillin resistant *Staphylococcus aureus* (MRSA) infections have been associated with dialysis treatment, prior antibiotic use, hospitalization in a burn unit or intensive care unit, prolonged hospitalization, previous hospitalization, and previous invasive procedures. Reservoirs for MRSA are similar to reservoirs for other resistant staphylococcal strains. Environmental surfaces in rooms of MRSA patients, as well as patient care equipment are frequently contaminated. However, the role of MRSA transmission from such contamination has not been well studied.

*Enterococcus* is another problematic organism identified as a source of nosocomial infections. As with *Staphylococcus aureus*, there has been a substantial increase in the incidence of resistance to isolates of *enterococcus* bacteria. According to the CDC, the overall proportion of enterococcal isolates resistant to vancomycin in the ICU of participating hospitals increased by 40% in 1999 compared to the mean rate of resistance over the previous years from 1994 through 1998.

The pathogens isolated from infections differ, primarily depending upon the type of surgidal procedure. In clean surgical procedures, in which the gastrointestinal, gynecological, and respiratory tracts have not been entered, *Staphylococcus aureus* from the exogenous environment or the patient's skin flora is the usual source of infection. According to data from the National Nosocomial Infections Surveillance System, there has been little change in the incidence and distribution of the pathogens isolated from infections in the last decade. However, more of these pathogens show antimicrobial drug resistance, especially methicillin-resistant *Staphylococcus aureus*.

Wound site infections are a major source of post-operative illness, accounting for many nosocomial infections. These infections number approximately 500,000 per year, among an estimated 27 million surgical procedures, infections that result in longer hospitalizations and higher costs. The average surgical site infection (SSI) prolongs the hospital stay by 7.3 days. These infections contribute to 42% of the extra charges attributed to nosocomial infections. In 1992, the extra costs were estimated at several thousand dollars per SSI infection.

On average, patients with surgical site infections incurred 4.6% extra ambulatory care visits than the patients who did not acquire these infections. In these hospitals, 0.62% to 1.9% of patients with surgical site infections died. These numbers highlight the tremendous human and financial costs that surgical site infections add to the healthcare system and therefore the importance of controlling them.

The antimicrobial effects of bisbiguanides have long been known. Chlorhexidine is the best known member of the class and has been used in the form of an aqueous solution or alcohol solution. Additionally, chlorhexidine has been marketed for many years in various formulas such as antibacterial hand washes and surgical scrub compositions for disinfection of hands and skin, disinfection of operation site, disinfection of medical instruments, disinfection of wounds, disinfection of operation room, patient's room, and the like. However, these formulations typically have included additional ingredients such as irritants, alcohols, and the like.

U.S. Pat. No. 6,107,261 to Taylor et al., issued Aug. 22, 2000, and its continuations-in-part, U.S. Pat. No. 6,204,230 to Taylor et al., issued Mar. 20, 2001 and U.S. Pat. No. 6,136,771 to Taylor et al., issued Oct. 24, 2000, disclose antibacterial compositions which contain an antibacterial agent at a percent saturation of at least 50%. The compositions further comprise, as solubility promoters, a surfactant and a hydric solvent, which may be an alcohol.

U.S. Pat. No. 5,776,430 to Osborne et al., issued Jul. 7, 1998, discloses a topical antimicrobial cleaner containing about 0.65-0.85% chlorhexidine and about 50-60% denatured alcohol, which is scrubbed onto and then rinsed off the skin.

European Patent Application 0604-848 discloses a gel comprising an antimicrobial agent, 40-90% by weight of an alcohol, and a polymer and thickening agent.

U.S. Pat. No. 4,956,170 to Lee, issued Sep. 11, 1990 relates to a high alcohol content antimicrobial gel composition which comprises various emollients and a humectant to protect the skin from the drying effects of the alcohol. In alcohol formulations, higher levels of alcohol are needed to provide instant kill against sensitive as well as resistant strains of bacteria.

U.S. Pat. No. 4,420,484 to Gorman et al. discloses a basic amino or ammonium antimicrobial agent (especially bisbiguanide, quaternary ammonium salt and bispyridine)-polyethylene glycol ester surfactant betaine and/or amine oxide surfactants antimicrobial skin cleansing compositions formulated with water, alcohol and various other ingredients.

U.S. Pat. No. 4,374,126 to Cardelli et al., teaches an alcoholic composition and method for forming a film where the composition comprises an alcohol soluble carboxylated polyacrylate which includes an antimicrobial agent, an adhesion promoter and a difunctional amide for crosslinking the polymer as the alcohol solvent evaporates. The film formed is thus resistant to body fluids, can remain on the skin for up to two days providing both initial and sustained anti-microbial activity.

U.S. Pat. Nos. 3,855,140 and 3,960,745 disclose the use of isopropyl alcohol while U.S. Pat. No. 4,919,837 discloses the use of lower alkanols such as ethanol or n-propanol. It is well known that alcohol defats the skin and may cause irritation thereof.

Cyclopentasiloxane (Velvesil™) is a silicone polymer that has been found useful in various cosmetic applications including antiperspirants, lotions, sunscreen, lipstick, shampoo, cuticle coat compositions, and hair conditioners, for example as disclosed in U.S. Pat. Nos. 6,444,745, issued Sep. 3, 2002; 6,531,540, issued Mar. 11, 2003; 6,538,061, issued Mar. 25, 2003; and 6,759,479, issued Jul. 6, 2004 all assigned to General Electric Company, Pittsfield, Mass. However, none of these patents disclose the use of cyclopentsiloxane as an ingredient in a non-alcoholic aqueous skin disinfectant for use as a surgical hand scrub, preoperative preparation, personnel hand wash, and the like.

Dyna-Hex 4®, a commercially available antimicrobial cleansing composition, manufactured and marketed by Xttrium Laboratories, consists of 4% chlorhexidine gluconate, cocamide DEA, fragrance POFL 147, glucono-delta-lactone, hydroxyethylcellulose, isopropyl alcohol, lauramine oxide, PEG-75 lanolin, purified water, and tridecyl alcohol. The isopropyl alcohol serves as a secondary vehicle for the other constituents.

There are two general problems associated with alcohol-based and/or containing disinfectants. First, the effective concentration of alcohol, generally regarded to be greater than about 60% weight of ethanol or its equivalent is irritating to the skin, causing dryness and consequent peeling and cracking. Due to the fact that chapped skin tends to be more susceptible to microbial contamination, repeated use of alcohol disinfectants can exacerbate the very problem they are intended to solve. Second, whereas alcohol can be an effective disinfectant, once it evaporates its antimicrobial activity is lost. Thus it has no residual antimicrobial effect.

Accordingly, a nonalcoholic antimicrobial cleansing composition which proves effective against Gram positive and Gram negative forms of bacteria and other microorganisms is highly desirable.

In recent years there has been an increased need and desire for effective antimicrobial products. The incidence of antimicrobial resistance has risen to dramatic levels. Yet at the same time there has been an increased need for products that are non-irritating and that can be applied quickly without the need for rinsing, i.e. a leave-on product.

SUMMARY OF THE INVENTION

The present invention relates to antimicrobial compositions that provide a substantial reduction in Gram-positive and Gram-negative bacteria without the use of alcohol as either a vehicle or a secondary active ingredient.

DETAILED DESCRIPTION OF THE INVENTION

The present invention is directed toward an antibacterial cleansing composition, that can be applied as a leave on product rather than a rinse off product. This product will effectively kill bacteria and other microorganisms and is mild on the skin such that it does not cause skin irritation or dryness. The antimicrobial cleansing compositions of the present invention have been found to reduce significantly the number of colony forming units (CFU's) of bacteria such as *Staphylococcus aureus* and the like and to do so without the use of an alcohol as either a secondary antimicrobial or a vehicle for the primary antimicrobial.

The essential ingredients of the nonalcoholic aqueous skin disinfectant composition are chlorhexidine gluconate, a silicone polymer, cyclopentasiloxane-$C_{30-45}$ alkyl cetearyl dimethicone crosspolymer (Velvesil™), and glycerin in a water-based matrix.

The present invention is both non-alcoholic, thus reducing its irritancy potential, and contains a unique silicone polymer, cyclopentasiloxane-$C_{30-45}$ alkyl cetearyl dimethicone crosspolymer, to further protect the skin from irritation. In addition to being non-alcoholic and non-irritating, the present invention can also be used as a leave-on product as opposed to a rinse off product. The majority of chlorhexidine gluconate based antimicrobials are rinse off products. The present invention can be used as a leave-on product.

The composition of the present invention is especially useful in personal care, disinfectants, surgical scrubs, healthcare personnel hand wash product, preoperative prep products, wound care agents and the like. Additionally, the present invention is skin friendly, nonalcoholic, nonirritating, and antimicrobial.

Chlorhexidine Gluconate:

ICI Laboratories of Great Britain synthesized chlorhexidine gluconate (1,1'-hexamethylene bis[5-(p-chlorophenyl biguanide]di-D-gluconate) in 1950. Since then, chlorhexidine has been considered the "gold standard" antibacterial agent and has been used as an antiseptic and disinfectant effective against a wide variety of Gram-positive and Gram-negative bacteria, fungi, yeast and select viruses. Chlorhexidine gluconate is also commonly known as chlorhexidine digluconate, a salt formed from chlorhexidine and gluconic acid. Chemically, chlorhexidine is a strong base and is most stable in its salt forms.

Chlorhexidine salts are readily adsorbed onto the cell walls of microorganisms, resulting in disruption of the cell wall integrity and leakage of intracellular contents. At low concentrations, chlorhexidine is a bacteriostatic agent, and at higher concentrations it becomes bacteriocidal. A primary benefit of chlorhexidine is its ability to kill bacteria on contact and remain non-toxic to mammalian cells.

The structural formula of chlorhexidine gluconate is:

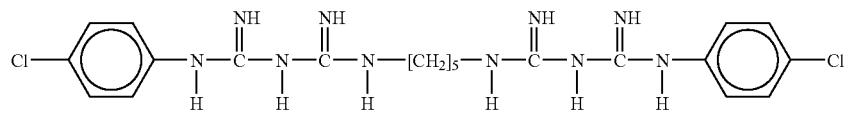

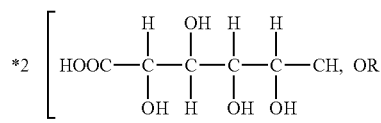

Chlorhexidine gluconate is considered the most persistent of all antimicrobial agents currently available. An important attribute of chlorhexidine gluconate is its strong affinity for skin. Most of the chlorhexidine gluconate applied to the surface of the skin attaches and remains, accounting for its ability to retain activity upon drying.

The concentration of chlorhexidine gluconate in the composition of the present invention is about 1 to 10% weight/weight ratio, preferably 2 to 6% weight/weight ratio, and most preferably 4% weight/weight ratio in a water-based matrix.

Chlorhexidine base may be used, however a salt of chlorhexidine which is soluble in the formulation is preferred. Preferred salts are the hydrochloride, acetate, and most preferably, the gluconate, due to its high water solubility and ease of adsorption.

Silicone Polymer:

Silicone polymer, as used according to the present invention relating to nonalcoholic skin disinfectant compositions, includes one or more of: polydimethylsiloxane polymer (Dow Corning 225 Silicone Fluid), dimethiconol fluid in dimethicone (Dow Corning 1403 Silicone Fluid), cyclomethicone and dimethicone copolyl (Dow Corning 3225C Silicone Fluid), silicone glycol (BASF 1066 DCG polyol), and most preferably, cyclopentasiloxane-$C_{30-45}$ alkyl cetearyl dimethicone crosspolymer (Velvesil™), as shown in (I).

Cyclopentasiloxane-$C_{30-45}$ alkyl cetearyl dimethicone crosspolymer is the creation of a copolymer network consisting of alkyl and polyether chains, in an organosilicone matrix incorporating various alkylsiloxanes. "Cyclopentasiloxane," which is defined herein to refer to the matrix incorporating cyclopentasiloxane-$C_{30-45}$ alkyl cetearyl dimethicone crosspolymer, as shown in I.

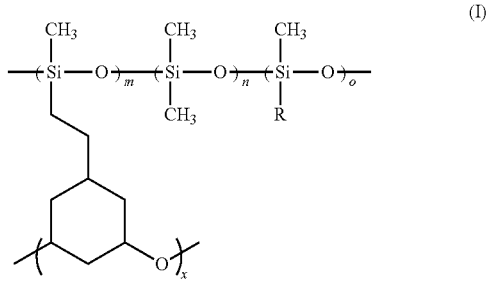

(I)

Cyclopentasiloxane is easily processed, is highly compatible with organic materials and provides emulsification benefits. Formulations containing cyclopentasiloxane range from low viscosity, sprayable emulsions to highly structured anhydrous gels. Cyclopentasiloxane is useful for a wide range of personal care products, including skin lotions and creams, sun care products, color cosmetics, shower gels, facial cleansers, hair conditioners and styling aids. Additionally, cyclopentasiloxane blends easily with other ingredients.

The concentration of the silicone polymer, cyclopentasiloxane, of the present invention may be employed to about 5% weight/weight ratio of the composition, preferably less than 0.1% weight/weight ratio, and most preferably 0.01% weight/weight ratio in a water-based matrix.

Glycerin:

Glycerin is a known humectant that has beneficial effects on skin conditioning due to its effects on the status of water in the outer layers of the stratum corneum. The conditioning is probably the result of glycerin interactions with the lipid proteins in the stratum corneum, altering their water binding and/or hydrophilic properties. Due to this phenomena, as glycerin interacts with the skin, water will tend to increase to form a reservoir in which water soluble active ingredients, such as chlorhexidine gluconate, can be dissolved and retained against wash off. Additionally, where the active ingredient is itself soluble in glycerin, the enhancement effect is further increased.

In addition to being a known humectant, glycerin can also be utilized as an anchoring agent. The anchoring agent of the present invention is selected from the group consisting of glycerin, propylene glycol, glyceraldehyde, dihydroxyacetone, 1,3-butylene glycol, 2,3-butylene glycol, erythritol, erythrose, erythrulose, ribose, sorbitol, mannitol, and inositol. Most preferably, the selected anchoring agent is glycerin.

Anchoring agent is defined herein as a hygroscopic agent that penetrates and remains in the upper layers of the skin (in other words a substantive agent), into which an active ingredient can be partitioned and retained with the anchoring agent against wash off. The anchoring agent provides for the slow release of an active ingredient, such as an anti-microbial.

The concentration of glycerin of the present invention may be employed to less than 1% weight/weight ratio and most preferably 0.25% weight/weight ratio in a water-based matrix.

The anchoring agent can be combined with other agents. Many polymeric materials with anchoring and substantive properties may be optionally combined with the anchoring agents described above, for example glycerin, to provide improved retention and slow release of soluble active ingredients.

Examples, of these agents include: octadecene-1/maleic anhydride copolymer, organofluorinated modified silicone resins, polyvinyl pyrrolidone, hydrogenated copolymers of styrene and butadiene, film forming copolymers, copolymers of eicosene and vinyl pyrrolidone, copolymer of hexadecane and vinyl pyrrolidone, cellulosic ethers, 2-hydroxyethyl methacrylate homopolymer, cocodimethyl ammonium salt of hydrolyzate of wheat protein, guar hydroxy propyltrimonium chloride, hydroxypropylcellulose, lauryldimonium hydroxypropyl hydrolyzed collagen, lauryldimonium hydroxypropyl hydrolyzed wheat protein, polyquaternium-24 and hyaluronic acid, soluble reticulin and soluble wheat protein, stearyldimonium hydroxypropyl hydrolyzed collagen, acrylic/acrylate copolymers, phenoxy dimethicone, dimethicone copolyol phosphate, polydecene/polybutene copolymer, polymethacrylamidopropyl trimonium chloride, polymethylalkyl siloxane, and the like.

Other Ingredients:

"Water-based matrix" means the use of Purified Water, USP, as an aqueous diluent that provides a safe non-toxic and non-irritating vehicle. The Purified Water, USP, is used to bring the weight/weight percentage of the composition to 100%.

If desired, the composition of the present invention may include a perfume to provide a pleasing scent. The perfume may be selected from, but is not limited to, a Neutrogena fragrance, fruit, wood, spice, and flower.

Additionally, the composition of the present invention may include a dye to provide a characteristic color. Merely as an example, dye may be selected from, but is not limited to, FD&C Blue No. 1, Red No. 2, Red No. 3, Red No. 40, Red No. 102, D&C Yellow No. 10, FD&C Green No. 3, and tar colors.

The pH of the composition of the present invention can be 5-7. If needed, the pH may be adjusted by addition of a suitable acidifying agent or alkalinizing agent, such as 6 N hydrochloric acid or 50% sodium hydroxide.

Uses:

A 4% weight/weight ratio of chlorhexidine gluconate has been found herein to be effective in reducing bacteria on human skin immediately upon contact with the skin surface, persistently up to 6 hours, and residually following. Also, it has been shown that reduction of skin flora can reduce the risk of certain types of nosocomial infections. Aqueous chlorhexidine gluconate formulas have been shown in the art to be effective against the following indicator organisms: *Escherichia coli, Staphylococcus epidermidis, Enterococcus faecium, Enterococcus faecalis, Pseudomonas aeuruginosa, Serratia marcescens, Candida albicans, Candida difficile.*

Additionally, 2-4% weight/weight ratio of chlorhexidine gluconate products of the present invention are useful for, but are not limited to, the following purposes: pre-injection, pre-operative prep, pre-catheter prep, catheter line insertion, central venous catheter, peripherally inserted central catheter, mid-line, dialysis, graft/fistula, arterial and femoral lines, swan gantz, site maintenance, chest tubes, surgical sites cleaning after stitching, minor surgical procedures, orthopedic pin placement, maintenance, and the like.

The composition of the current invention will reduce colony forming units/cm$^2$ on the skin by giving at least a 3.0 $\log_{10}$ reduction that lasts up to several (>5) hours after application, and up to a 2.0 $\log_{10}$ reduction within 1 minute of use. To achieve this result, the compositions of the current invention can be applied as a single application or successive applications over several days.

Abbreviations and Definitions

"Nonalcoholic" is defined herein to mean that the composition contains less than about 10% alcohol by weight. In certain specific embodiments of the invention, nonalcoholic can also mean that the composition contains less than about 5%, about 2%, or about 1% alcohol by volume. Preferably, nonalcoholic means that the composition contains less than about 0.5% alcohol by volume. Most preferably, nonalcoholic means that the composition contains no alcohol.

"Anti-microbial" and "disinfectant" are defined herein to mean an agent that inhibits the growth of, or kills, organisms including bacteria, protozoans, viruses, prions, yeast, fungi, or other infectious agents, and has increased substantive properties when combined with the agents above, meaning it penetrates into the skin providing long lasting anti-microbial activity even after wash off.

"Healthcare worker" is defined herein to mean a physician, nurse, nurse's assistant, anesthesiologist, emergency medical technician, pre-operative assistant, post-operative assistant, and the like.

"Non-Irritating" is defined as meeting the characteristics that patients receiving the present invention do not develop erythema or more distressing forms of skin irritation.

"Leave-On" is defined herein to mean a product that is applied to the skin and left to dry without the need of a water rinse.

EXAMPLES

Example 1

Preferred Composition of the Present Invention

| Ingredient | Percentage of Ingredient (weight/weight) |
|---|---|
| Chlorhexidine Gluconate | 4% |
| Cyclopentasiloxane - C$_{30-45}$ Alkyl Cetearyl Dimethicone Crosspolymer | 0.01% |
| Glycerin, USP | 0.25% |
| Purified Water, USP | 95.74% |

Example 2

Test for Preoperative Skin Preparations

Prior to surgery or other invasive procedures, the patient's skin must be treated with topical antimicrobial products (Pre-Operative Skin Preparations) to prevent nosocomial infections by reducing the number of microorganisms on the skin. There are several procedures available for evaluating the efficiency of antibiotic skin compositions. For example, Tentative Final Monograph (TFM) for Health-Care Antiseptic Drug Products (Vol. 59, No. 116, Jun. 17, 1994) describes an in vivo procedure for evaluating this type of product as well as expected performance criteria. When a new product is tested, a predicate preoperative skin preparation must be included in the study as a positive control.

The antimicrobial effectiveness potential of a single test sample of a 4% nonalcoholic chlorhexidine gluconate (CHG) composition was evaluated for use as patient preoperative skin preparations. This evaluation was conducted based on methodology specified by the Food and Drug Administration Office of Drug Evaluation and Research. A minimum of 6 human subjects were employed utilizing unilateral product applications assuring that the test product was evaluated on sites as described in the following table.

| Test Sample | Number of Evaluations on Groin |
|---|---|
| 4% Nonalcoholic Chlorhexidine Gluconate Composition | 6 |

A 4% nonalcoholic chlorhexidine gluconate (CHG) composition was evaluated at various groin sites for immediate antimicrobial effect by sampling at 30 seconds, 10 minutes±30 seconds and 6 hours±30 minutes after completion of application. All product applications were performed using randomized placement.

A) Neutralization:

The objective of this evaluation was to determine the ability of the sampling solutions to completely neutralize the active ingredients contained in a 4% nonalcoholic chlorhexidine gluconate (CHG) composition cleanser when applied to the groin of test subjects without exhibiting toxicity to the marker organism. The test microorganism used for the neutralization study was *Staphylococcus epidermidis*, ATCC 12228, a common skin bacterium.

B) Procedures:

Pre-Test Period:

A period of at least two weeks prior to the first baseline sampling was designated the "pre-test" period. During this time subjects were instructed to use only personal hygiene products supplied by the Investigator for personal hygiene (soaps, shampoos, deodorants, etc.) and was told to avoid skin contact with solvents, acids, and bases. Subjects were prohibited from using UV tanning lamps, and from bathing in chemically treated pools and/or hot tubs. Additionally, the subjects were not be allowed to bathe or shower forty-eight hours prior to being sampled. They were allowed to take sponge baths; however, they were not allowed to disturb the test sites.

Subjects were not allowed to shave the anatomical sites within five days prior to being treated with a 4% nonalcoholic chlorhexidine gluconate (CHG) composition. This regimen allowed for the stabilization of the normal microbial flora of the skin.

Baseline Week:

The week following the pre-test period will constitute the baseline week. Subjects were not allowed to shower within 48 hours of being sampled. All subjects were sampled for screening the baseline at least 72 hours prior to treatment with a 4% nonalcoholic chlorhexidine gluconate (CHG) composition.

Samples taken from the two contralateral groin sites were collected. Based upon an adequate screening the baseline count on contralateral groin sites, a subject was eligible to continue the study. Criteria for acceptance of screening counts was at least $1.0 \times 10^5$ colony forming units/cm$^2$ on contralateral sites in the groin region. A second and final baseline sample using the same criteria as for screening baseline was collected at each test area prior to being prepped on the day of treatment.

Post-treatment count data was excluded from the data analysis if they were derived from any area that failed to exhibit a level of bacteria at the second baseline sampling sufficient ($1.0 \times 10^5$ colony forming units/cm$^2$ on contralateral sites in the groin region) to permit detection of a 3.0 $\log_{10}$ reduction in the groin region sites.

The table below summarizes the minimum baseline criteria for the test sites along with the minimum effective $\log_{10}$ reduction criteria stipulated by the FDA.

| Anatomical Site | Minimum Baseline | Minimum $\log_{10}$ Reduction |
|---|---|---|
| Groin | $1.0 \times 10^5$ CFU/cm$^2$ | 3.0 $\log_{10}$ @ 10 minutes |

All sample sites that required clipping were clipped at least 48 hours prior to test day. All sampling were performed using the cylinder sampling technique.

Test Period:

Prior to sampling, the subjects were questioned regarding their adherence to protocol restrictions. Subjects were visually examined again (by a technician) at the anatomical sampling sites to ensure no evidence of injury or dermatoses were present.

Randomization: Test areas on each subject's groin regions were delineated according to a computer generated randomization schedule to receive a 4% nonalcoholic chlorhexidine gluconate (CHG) composition on one side. Randomization was balanced between both the left and right sides. Treatment day baseline and post prep sampling sites were randomized within each test area.

Blinding: The 4% nonalcoholic chlorhexidine gluconate (CHG) composition was not blinded from the investigator because of the obvious difference in the products. The investigator that treated the subject was not involved in bacterial enumeration and counting the plates of that particular subject.

The dimensions of each treatment area were 2"×5" on the upper/inner part of the thigh below the inguinal ligament. Four sampling sites were delineated within each treatment area. Based upon the earlier design, the groin region was sampled for the final baseline (second baseline). The appropriate areas were prepped using a 4% nonalcoholic chlorhexidine gluconate (CHG) composition. The sites were then sampled at 30 seconds, 10 minutes±30 seconds, and 6 hours±30 minutes.

For the 6 hour±30 minutes sites, sterile gauze pads were placed over the prepped areas to aid in the prevention of microbial contamination. The gauze pads were held in place with an occlusive sterile dressing. All samples were taken from sites using the cylinder sampling technique.

Microbiological Methods:

Sample Collection:

Quantitative cultures were obtained by a modification of the cylinder sampling technique of Williamson and Kligman (J. Invest. Dermatol. 45:498-503, 1965). A sterile scrubbing cup (3.8 cm$^2$, internal area, height approximately 2.54 cm) was held firmly to the skin over the site to be sampled. Three ml of scrub solution containing neutralizers were placed into the cup, and the area scrubbed with moderate pressure for one minute using a sterile rubber "policeman." The scrub solution was aspirated and replaced with 3.0 ml of fresh solution and the scrub repeated. The two aliquots were pooled. These procedures were used for all baseline samples and treatment samples. Aliquots of the pooled scrub solutions were diluted in 10-fold steps, using Butterfield's Phosphate Buffered Dilution water containing neutralizers as the diluent.

Enumeration of Microorganisms:

One ml aliquots of appropriate dilutions were plated in duplicate in 15-20 ml soybean-casein digest agar pour plates containing appropriate neutralizers within 30 minutes of the sampling. After 72±4 hours aerobic incubation at 30±2° C., colonies were counted and viable cells in the original sample were calculated based on the procedure Counting Colonies on Plates and Reporting Results, Standard Methods For Evaluation of Dairy Products, 14th Ed. American Public Health Association, Washington D.C. The plates were stored under refrigeration for up to 48 hours prior to counting. The average number of microorganisms recovered per cm$^2$ of skin were determined and reported.

To convert the volume of sample collected into colony forming units/cm$^2$ of skin, the following formula was used:

$$R = \log_{10}\left[\frac{F\left(\frac{\Sigma c_1}{n}\right)10^{-D}}{A}\right]$$

Where:

R=the average colony forming units count in $\log_{10}$ scale per cm$^2$ of skin F=total ml of stripping fluid added to the sampling cylinder; F=6.0 ml c/n=average of the duplicate colony counts used for each sample collected
D=dilution factor of the plates counted
A=inside area of the sampling cylinder (3.8 cm$^2$)

Growth Promotion Control:

For each batch of plating medium, soybean-casein digest agar (or equivalent) containing 0.5% polysorbate 80 and 0.07% lecithin, fewer than 100 colony forming units of *Staphylococcus epidermidis*, ATCC 12228 was inoculated in a single plate pour plate. A 20-26 hour aged culture of *Staphylococcus epidermidis* was serially diluted in dilution fluid. The colony forming units added were confirmed in duplicate spread plates. The plates were incubated for 72±4 hours at 30±2° C.

Adverse Events:

All adverse events, regardless of severity or the causal/effect relationship, were recorded. The severity of the effect was noted as "Mild," meaning awareness of signs or symptom, but easily tolerated; "Moderate," meaning discomfort to a degree as to cause interference with normal daily life activities and/or requiring medication; and "Severe," meaning incapacity with inability to work or do usual daily life activities and requiring medical attention/intervention.

Causal Relations of Adverse Event/Experience:

When determining the causal/effect relationship to the 4% nonalcoholic chlorhexidine gluconate composition, the relationship was described as "None," "Possible," "Probable," or "Definite." The following definitions were utilized:

| | |
|---|---|
| None | No association to the test article. Related to other etiologies such as concomitant medications or conditions or subject's known clinical state. |
| Possible | Uncertain association. Other etiologies are also possible. |
| Probable | Clear-cut association with improvement upon withdrawal of the test article. Not reasonably explained by the subject's known clinical state but not an anticipated event. |
| Definite | An adverse event with a clear-cut temporal association and laboratory confirmation if possible. |

Serious Adverse Event/Experience:

A Serious Adverse Event/Experience is any adverse experience occurring at any dose that results in any of the following outcomes: death; a life-threatening adverse drug experience; inpatient hospitalization or prolongation of existing hospitalization; a persistent or significant disability/incapacity; and congenital anomaly/birth defect.

Unexpected Adverse Event/Experience:

An Unexpected Adverse Event/Experience is any adverse drug event/experience not described above.

Follow-Up:

If an adverse event/experience occurred, the subject was referred to the nearest acute care facility for treatment. Serious or Unexpected Drug Event/Experience was followed to resolution. Any adverse event was documented on an Adverse Event Report.

Anticipated Reactions:

The risks associated with this test were primarily related to application of a 4% nonalcoholic chlorhexidine gluconate (CHG) composition. Tape reactions were also possible. Mild to heavy erythema, swelling, itching, cracking, peeling, or in rare cases, blistering and or an allergic reaction might occur. Occurrence of any of these events were considered an "Adverse Event" and were documented in the study record.

Data Analysis:

The analyses outlined below was conducted on the data generated. Raw data (colony forming units/ml) was converted to $\log_{10}$ colony forming units/cm$^2$. Counts of less than 1 colony forming unit/cm$^2$ were treated as 1 colony forming unit/cm$^2$ such that the log transformation was zero. Log reductions were calculated by subtracting the post treatment log counts from the treatment day baseline counts obtained. Only subjects who met the minimum inclusion criteria for levels of bacteria on the treatment day of the study were included in the analysis with the following exception: lab accidents resulting in contaminated samples. If there were missing data at some but not all time points, data from the available times were included in the analysis. Any subject with missing data was not included in the data analysis. The subject with missing data was replaced with a new subject.

Example 3

Prepping Technique for 4% Nonalcoholic Chlorhexidine Gluconate Composition

The groin area was prepped with a 4% nonalcoholic chlorhexidine gluconate composition by the following steps: a) five milliliters of a 4% nonalcoholic chlorhexidine gluconate (CHG) composition was applied onto a sterile gauze pad; b) a 4% nonalcoholic chlorhexidine gluconate (CHG) composition was applied to the treatment area for 2 minutes and the area was dried with a sterile towel or sterile gauze; and c) steps a-b were repeated. Contact timed began after the site dried a second time.

Example 4

Neutralizer Validation Procedure

The objective of this evaluation was to determine the ability of the sampling solutions to completely neutralize the active ingredients contained in a 4% nonalcoholic chlorhexidine gluconate (CHG) composition cleanser when applied to the abdomen of test subjects without exhibiting toxicity to the marker organism.

One subject participated in this study. Subject met the inclusion and exclusion criteria of the protocol to which this neutralizer validation was to be performed. The neutralization subject did not require a minimum bacterial count and he/she was told to avoid topical and systemic antimicrobials for 14 days prior to the treatment day. For one subject, a 4% nonalcoholic chlorhexidine gluconate composition was applied to both side of the abdomen.

The test organism was *Staphylococcus epidermidis* ATCC 12228. The culture was prepared from an overnight (24±2 hr.) broth culture grown at 30±2° C. in an appropriate medium which contained approximately $10^8$-$10^9$ colony forming unit/ml.

The overnight suspension was serially diluted with Butterfield's phosphate buffered water (PBW) and an appropriate concentration for inoculation of the test samples was achieved.

Neutralization Effectiveness Control: a) Samples were taken from the abdomen with scrub solution containing neutralizers. The subject number, location of the prep application, location of the sites sampled within the prep area, and the time of sample collection were documented; b) the abdomen test areas were marked using a sterile 2"×5" template; c) after the test areas were marked, each site was prepped with three 70% isopropyl alcohol swabs for a total of one minute and waited for the site to dry; d) the site was prepped with a 4% nonalcoholic chlorhexidine gluconate composition; e) the tile scrub technique was used, at 30 seconds post prep the sample was collected using scrub solution containing neutralizers; f) each pooled sample (approximately 6 ml) was mixed on a Vortex-type mixer before transferring 5 ml to a clean tube. The tube was immediately inoculated with approximately 100-500 colony forming units/ml; g) post-inoculation 1 ml aliquot of inoculated sample was spread plated immediately (<1 minute) and at 30 minutes (±2 minutes) using trypticase soy agar containing neutralizers. (0.1 ml aliquots per plate, one ml across 10 plates in duplicates). The plates were incubated at 30±2° C. for 48±2 hours.

Number Controls: Diluted inoculum was added into a tube containing 5.0 ml of sampling solution without neutralizers which yielded final inoculum concentrations of ~100-500 colony forming units/ml. Duplicate 1.0 ml aliquots were plated immediately (<1 minute) and 30 minutes (±2 minutes) post inoculation in the same manner as c) above except trypticase soy agar was used without neutralizers.

Toxicity Control: a) Diluted inoculum was added into a tube that contained 5.0 ml of sampling solution and neutralizers which yielded final inoculum concentrations of ~100-500 colony forming units/ml. Duplicate 1.0 ml aliquots were plated immediately (<1 minute) and 30 minutes (±2 minutes) post inoculation in the same manner as c) above except using trypticase soy agar containing neutralizers; b) the plates were enumerated and colony forming units/ml for each sample were calculated; c) the data was converted to $\log_{10}$ to colony forming units/ml; d) data evaluation and recovery for each of the samples was expressed as $\log_{10}$ colony limiting units/ml.

Neutralizer Effectiveness: If the $\log_{10}$ colony forming units/ml of the antiseptic sample was not more than 0.3 logs less than the Numbers Control, the neutralizer was considered effective.

Neutralizer Toxicity: If the Toxicity Control (TC) was not more than 0.3 logs less than the Numbers Control sample, the sampling solutions were considered non-toxic.

The neutralization effectiveness control, number controls, and toxicity control provided assurance that the test organism was not adversely affected by the sampling solutions or procedure.

Summary and Conclusions

The FDA *Tentative Final Monograph for Health-Care Antiseptic Drug Products; Proposed Rule*, published in the Federal Register of Jun. 17, 1994, required a 3.0 $\log_{10}$ reduction in colony forming units/cm² of skin within 10 minutes after drug application. The count must not exceed the test-day baseline after six hours. The $\log_{10}$ reductions in colony forming units/cm² of skin on the groin sites were achieved by a 4% nonalcoholic chlorhexidine gluconate (CHG) composition and exceeded the FDA's proposed 3.0 $\log_{10}$ reduction criteria for the groin site at the 10 minute sampling interval. The colony forming units/cm² recovered at the 6-hour sampling interval did not exceed the test-day baseline.

Example 5

Average Log $\log_{10}$ Reduction

| Groin Site - Average Log $\log_{10}$ Reduction (using test-day baseline) | |
|---|---|
| Sampling Interval | Test Article Identification 4% Nonalcoholic Chlorhexidine Gluconate Composition |
| 30 seconds | 3.38 |
| 10 minute | 3.68 |
| 6 hour | 3.37 |

Example 6

Subject Disposition

| | |
|---|---|
| Enrollment Summary | 10 subjects |
| Passing Screening Baseline Summary (on groin) | 8 subjects |
| Failing Screening Baseline Summary (on groin) | 2 subjects |
| Treatment Summary | 8 subjects |
| Passing Treatment Baseline Summary (on groin) | 6 subjects |
| Failing Treatment Baseline Summary (on groin) | 2 subjects |

Example 7

An Evaluation to Determine the Irritancy Potential of One Test Product Over the Course of a 24 Hour Exposure The purpose of this evaluation was to determine the irritation/hypoallergenic potential of a 4% nonalcoholic chlorhexidine gluconate (CHG) composition after a single 24 hour patch exposure to the skin of human subjects. The irritation potential of a 4% nonalcoholic chlorhexidine gluconate (CHG) composition was determined using 21 volunteer human subjects over the course of a 24 hour challenge period. A 4% nonalcoholic chlorhexidine gluconate (CHG) composition was applied directly to the inner surface of the upper arm. The test site was evaluated visually prior to product application and 24 hours post-4% nonalcoholic chlorhexidine gluconate (CHG) composition application.

Inclusion Criteria:

A sufficient number of overtly healthy subjects at least 18 years of age were admitted into the study to ensure that 21 subjects completed the study. Insofar as possible, the group of subjects selected was of mixed sex, age, and race. The skin of the upper inner arms of subjects were free from clinically evident dermatoses, injuries, open wounds, tattoos, and/or any other disorders that may have compromised the subject and the study.

Exclusion Criteria:

Subjects were not allowed to use tanning beds, or soaking in pools or tubs, showering, or washing the test sites during the 24 hour test period. Subjects were excluded from the study that used topical medication or had known allergies or sensitivities to inks, latex, commonly used cosmetic products, isopropyl alcohol, or chlorhexidine gluconate. If any subjects had a physical condition, such as a current or recent severe illness, asthma, diabetes, hepatitis, cancer, or any immunocompromised conditions such as AIDS (or HIV positive), they were excluded. Any pregnancies, active skin rashes, dermatitis, use of drug delivery patches, any medical condition, that in the opinion of the investigator, should preclude participation, and any unwillingness were grounds for exclusion.

Test Period:

All visual evaluations were performed by trained evaluators. Visual assessments of the subjects' test site was made for baseline. Approximately 25 μl of a 4% nonalcoholic chlorhexidine gluconate (CHG) composition was applied directly to a 0.25 square inch site (0.5 inch on a side), randomly assigned to the skin of the inner, upper arm. The 4% nonalcoholic chlorhexidine gluconate (CHG) composition was allowed to dry on the skin for at least 15 minutes, after which the site was pat-dried with a paper towel, if necessary. The site was marked with a sterile skin marker if the site is not apparent.

Subjects were allowed to leave the laboratory. Prior to leaving the laboratory, subjects were instructed not to sun-tan, use tanning beds, soak in pools or tubs, shower, or wash the test site during the 24 hour test period. Twenty-four hours±1 hour post-product application, subjects returned to the laboratory, and the test site was scored for signs of irritancy.

Visual evaluations were performed prior to product application and 24 hours post-product application and the test site was graded for irritation on the basis of descriptions provided in Example 8. Any exposure site graded with a score of 6 or 7 was considered an Adverse Event.

Example 8

Grading Scale for Visual Evaluation of Skin Condition

| GRADE | DESCRIPTION |
| --- | --- |
| 0 | No evidence of irritation |
| 1 | Minimal erythema, barely perceptible |
| 2 | Definite erythema, readily visible; minimal edema or minimal papular response |
| 3 | Erythema and papules |
| 4 | Definite edema |
| 5 | Erythema, edema, and papules |
| 6* | Vesicular eruption |
| 7* | Strong reaction spreading beyond test site |

*was considered an Adverse Event

Following the final visual evaluation, the test site was washed with soap and water and/or 70% isopropyl alcohol.

Summary and Conclusions

The preliminary results of this study indicated that a 4% nonalcoholic chlorhexidine gluconate (CHG) composition did not cause irritation or induce a hypoallergenic response in the test subjects over a single 24 hour patch exposure to the skin. All 21 patients received a grade of 0, indicating that there was no evidence of irritation.

All patents, patent applications and publications cited in this application are to hereby incorporated by reference in their entirety for all purposes to the same extent as if each individual patent, patent application or publication were so individually denoted.

Although certain embodiments and examples have been described in the detail above, those having ordinary skill in the art will clearly understand that many modifications are possible in the embodiments and examples without departing from the teachings thereof. All such modifications are intended to be encompassed within the below claims of the invention.

What is claimed is:

1. A nonalcoholic aqueous skin disinfectant composition, comprising: chlorhexidine gluconate, a silicone polymer and an anchoring agent in a water-based matrix, wherein chlorhexidine gluconate is the sole active ingredient and is present in a weight/weight ratio of 2-6% in the water-based matrix, the silicone polymer is present in a weight/weight ratio of 0.05% in the water-based matrix, and the anchoring agent is present in a weight/weight ratio of less than 1% in the water-based matrix.

2. The composition of claim 1, wherein chlorhexidine gluconate is present in a weight/weight ratio of 4% in the water-based matrix.

3. The composition of claim 1, wherein the silicone polymer is selected from the group consisting of polydimethylsiloxane polymer, dimethiconol fluid in dimethicone, cyclomethicone and dimethicone copolyl, silicone glycol, and cyclopentasiloxane-$C_{30-45}$ alkyl cetearyl dimethicone crosspolymer.

4. The composition of claim 3, wherein the silicone polymer is cyclopentasiloxane-$C_{30-45}$ alkyl cetearyl dimethicone crosspolymer.

5. The composition of claim 4, wherein cyclopentasiloxane-$C_{30-45}$ alkyl cetearyl dimethicone crosspolymer is present in a weight/weight ratio of 0.01% in the water-based matrix.

6. The composition of claim 1, wherein the anchoring agent is selected from the group consisting of glycerin, propylene glycol, glyceraldehyde, dihydroxyacetone, 1,3-butylene glycol, 2,3-butylene glycol, erythritol, erythrose, erythrulose, ribose, sorbitol, mannitol, and inositol.

7. The composition of claim 6, wherein the anchoring agent is glycerin.

8. The composition of claim 6, wherein glycerin is present in a weight/weight ratio of 0.25% in the water-based matrix.

9. The composition of claim 1, further comprising a coloring additive or a fragrance additive.

10. The composition of claim 1 that is a leave-on product.

11. A method for disinfecting skin, comprising:
applying the skin disinfectant composition of claim 1 to the skin of a patient, wherein the composition comprises chlorhexidine gluconate, a silicone polymer and anchoring agent in a water-based matrix.

12. The method of claim 11, wherein the composition is used as a leave-on product.

13. The composition of claim 11, wherein the composition is optionally rinsed off.

14. A preoperative nonalcoholic aqueous skin disinfectant composition, comprising: chlorhexidine gluconate, a silicone polymer and anchoring agent in a water-based matrix, wherein the chlorhexidine gluconate gluconate is the sole active ingredient and is present in a weight/weight ratio of 2-6% in the water-based matrix, the silicone polymer is present in a weight/weight ratio of 0.05% in the water-based matrix, and the anchoring agent is present in a weight/weight ratio of less than 1% the water-based matrix, wherein the composition causes at least a 3-log reduction of bacteria after 4 minutes of contact with the skin.

15. A nonalcoholic aqueous hand wash disirffectant composition, comprising: chlorhexidine gluconate, a silicone polymer and anchoring agent in a water-based matrix, wherein the chlorhexidine gluconate gluconate is the sole active ingredient and is present in a weight/weight ratio of 2-6% in the water-based matrix, the silicone polymer is present in a weight/weight ratio of 0.05% in the water-based matrix, and the anchoring agent is present in a weight/weight ratio of less than 1% the water-based matrix, wherein the composition causes at least a 2-log reduction of an indicator organism within 5 minutes after the first wash.

16. The composition of claim 15, wherein the indicator organism is selected from the group consisting of: *Escherichia coli, Staphylococcus epidermidis, Enterococcus faecium, Enterococcus faecalis, Pseudomonas aeruginosa, Serratia marcescens, Candida albicans, Candida difficile.*

17. The composition of claim 15, wherein the composition causes at least a 3-log reduction of an indicator organism within 5 minutes of the tenth wash.

18. The composition of claim 17, wherein the indicator organism is selected from the group, consisting of: *Escherichia coli, Staphylococcus epidermidis, Enterococcus faecium, Enterococcus faecalis, Pseudomonas aeuruginosa, Serratia marcescens, Candida albicans, Candida difficile.*

19. A nonalcoholic aqueous surgical hand scrub disinfectant composition, comprising: clflorhexidine gluconate, a silicone polymer and anchoring agent in a water-based matrix, wherein the chlorhexidine gluconate is the sole active ingredient and is present in a weight/weight ratio of 2-6% in the water-based matrix, the silicone polymer is present in a weight/weight ratio of 0.05% in the water-based matrix, and the anchoring agent is present in a weight/weight ratio of less than 1% in the water-based matrix, wherein the composition causes at least a I-log reduction of a microbial flora on the hand within 1 minute on day one.

20. The composition of claim 19, wherein the composition causes at least a 2-log reduction of the microbial flora on the hand within 1 minute of use on the second day.

21. The composition of claim 19, wherein the composition causes at least a 3-log reduction of the microbial flora on the hand within 1 minute of use by the end of the fifth day.

22. The composition of claim 19, wherein the composition causes a suppression of a bacterial growth on the hand for at least 6 hours on the first day.

23. A method of disinfecting skin prior to surgery, comprising: applying to the skin a nonalcoholic aqueous disinfectant composition, wherein the composition comprises chlorhexidine gluconate is the sole active ingredient and, a silicone polymer and anchoring agent in a water-based matrix, wherein the chlorhexidine gluconate is present in a weight/weight ratio of 2-6% in the water-based matrix, the silicone polymer is present in a weight/weight ratio of 0.05% in the water-based matrix, and the anchoring agent is present in a weight/weight ratio of less than 1% in the water-based matrix.

24. A method of disinfecting hands by applying a nonalcoholic aqueous disinfectant composition, comprising: chlorhexidine gluconate, a silicone polymer and anchoring agent in a water-based matrix, wherein the chlorhexidine gluconate is the sole active ingredient and is present in a weight/weight ratio of 2-6% in the water-based matrix, the silicone polymer is present in a weight/weight ratio of 0.05% in the water-based matrix, and the anchoring agent is present in a weight/weight ratio of less than 1% in the water-based matrix, wherein the composition causes at least a 2-log reduction of an indicator organism within 5 minutes after the first wash.

25. The method of claim 24, wherein the indicator organism is selected from the group, consisting of: *Escherichia coli, Staphylococcus epidermidis, Enterococcus faecium, Enterococcus faecalis, Pseudomonas aeuruginosa, Serratia marcescens, Candida albicans, Candida difficile.*

26. The method of claim 24, wherein the composition causes at least a 3-log reduction of an indicator organism within 5 minutes of the tenth wash.

27. The method of claim 26, wherein the indicator organism is selected from the group, consisting of: *Escherichia coli, Staphylococcus epidermidis, Enterococcus faecium, Enterococcus faecalis, Pseudomonas aeuruginosa, Serratia marcescens, Candida albicans, Candida difficile.*

28. A method of disinfecting the hands of a healthcare worker prior to the healthcare worker participating in a surgical procedure, comprising applying a nonalcoholic aqueous disinfectant composition, comprising: chlorhexidine gluconate, a silicone polymer and anchoring agent in a water-based matrix, wherein the chlorhexidine gluconate is the sole active ingredient and is present in a weight/weight ratio of 2-6% in the water-based matrix, the silicone polymer is present in a weight/weight ratio of 0.05% in the water-based matrix, and the anchoring agent is present in a weight/weight ratio of less than 1% in the water-based matrix, wherein the composition causes at least a I-log reduction of a microbial flora on the hand within 1 minute on day one.

29. The method of claim 28, wherein the composition causes at least a 2-log reduction of the microbial flora on the hand within 1 minute of use on the second day.

30. The method of claim 28, wherein the composition cause at least a 3-log reduction of the microbial flora on the hand within 1 minute of use by the end of the fifth day.

31. The method of claim 28, wherein the composition causes a suppression of a bacterial growth on the hand for at least 6 hours on the first day.

\* \* \* \* \*

UNITED STATES PATENT AND TRADEMARK OFFICE
CERTIFICATE OF CORRECTION

PATENT NO. : 8,173,147 B2  
APPLICATION NO. : 12/192502  
DATED : May 8, 2012  
INVENTOR(S) : Kevin Scott Creevy It is certified that error appears in the above-identified patent and that said Letters Patent is hereby corrected as shown below:

Column 16, Claim 14, ln. 44, "chlorhexidine gluconate gluconate" should read "chlorhexidine gluconate";

Column 16, Claim 15, ln. 52, "hand wash disirffectant" should read "hand wash disinfectant";

Column 17, Claim 19, ln. 10, "clflorhexidine gluconate" should read "chlorhexidine gluconate";

Column 17, Claim 19, ln. 18, "I-log reduction" should read "1-log reduction"; and Column 18, Claim 28, ln. 32, "I-log reduction" should read "1-log reduction".

Signed and Sealed this  
Twenty-eighth Day of August, 2012

David J. Kappos  
*Director of the United States Patent and Trademark Office*